(12) United States Patent
Watanabe et al.

(10) Patent No.: US 7,549,586 B2
(45) Date of Patent: Jun. 23, 2009

(54) OPTICAL MEASUREMENT SYSTEM AND SAMPLE OPTICAL PROPERTY MANAGEMENT METHOD

(75) Inventors: Koji Watanabe, Edogawa-ku (JP); Toru Kobayashi, Ibaraki (JP); Masao Nakamuro, Takarazuka (JP); Naoki Sagisaka, Tondabayashi (JP)

(73) Assignee: Konica Minolta Sensing, Inc., Sakai-Shi (JP)

( * ) Notice: Subject to any disclaimer, the term of this patent is extended or adjusted under 35 U.S.C. 154(b) by 213 days.

(21) Appl. No.: 11/166,883

(22) Filed: Jun. 24, 2005

(65) Prior Publication Data

US 2006/0000885 A1    Jan. 5, 2006

(30) Foreign Application Priority Data

Jun. 28, 2004   (JP)   ............................. 2004-189687

(51) Int. Cl.
*G06K 7/10* (2006.01)
(52) U.S. Cl. .................... 235/470; 235/454; 235/383
(58) Field of Classification Search ................ 235/470, 235/454, 492, 375, 383; 382/123
See application file for complete search history.

(56) References Cited

U.S. PATENT DOCUMENTS 6,434,257 B1 * 8/2002 Mohan et al. ............... 382/110
6,529,855 B1 * 3/2003 Gu .............................. 702/155
6,836,325 B2 * 12/2004 Maczura et al. ............. 356/328
6,845,910 B2 * 1/2005 Gu et al. ...................... 235/454
7,190,257 B2 * 3/2007 Maltseff et al. ........... 340/10.51
2004/0220860 A1 * 11/2004 Persky et al. .................. 705/23

FOREIGN PATENT DOCUMENTS

JP         06-041864 A     2/1994

* cited by examiner

*Primary Examiner*—Ahshik Kim
(74) *Attorney, Agent, or Firm*—Sidley Austin LLP

(57) ABSTRACT

An optical measurement system which manages whether an optical property of a sample falls within a predetermined management range. The optical measurement system has a measuring device for measuring the optical property value of the inspected sample, a reader for reading an attribute identification information of an identification tag attached to the sample, and a storage section for storing optical property management information concerning a plurality of kinds of samples each in a manner corresponding to attribute identification information of each sample. A controller in the optical measurement system reads out from the storage section the optical property management information corresponding to the attribute identification information of the sample read by said reader, and compares the optical property management information with the optical property value of the sample, and then determines whether the optical property value falls within an allowable range in the optical property management information.

13 Claims, 11 Drawing Sheets

Fig.5

| | reference model number | reference color value | | | Company A management width | | | | | | | | | |
|---|---|---|---|---|---|---|---|---|---|---|---|---|---|---|
| | | | | | ΔL* | | Δa* | | Δb* | | ΔE* | | | |
| NO. | | L* | a* | b* | upper limit (+) | lower limit (-) | upper limit (+) | lower limit (-) | upper limit (+) | lower limit (-) | upper limit (+) | | | |
| 1 | 1101 | 27.41 | 26.94 | 16.33 | 1.0 | 1.0 | 1.0 | 1.0 | 1.0 | 1.0 | 1.0 | | | |
| 2 | 1102 | 27.41 | 28.46 | 34.11 | 1.5 | 1.5 | 0.5 | 0.5 | 0.5 | 0.5 | 1.2 | | | |
| 3 | 1105 | 27.41 | 36.18 | 21.93 | 0.8 | 0.8 | 0.8 | 0.8 | 0.8 | 0.8 | 1.5 | | | |
| 4 | 1308 | 27.41 | ... | ... | ... | ... | ... | ... | ... | ... | ... | | | |
| 8 | 1401 | 27.41 | 20.05 | 15.18 | 1.0 | 1.0 | 0 | 10.00 | 0 | 12.0 | 16.0 | | | |
| ... | | | | | | | | | | | | | | |

TB  KK  KS  FL  KH

OPTICAL MEASUREMENT SYSTEM AND SAMPLE OPTICAL PROPERTY MANAGEMENT METHOD

CROSS-REFERENCE TO RELATED APPLICATION

This application is based on Japanese Patent Application No. 2004-189687 filed in Japan on Jun. 28, 2004, the entire content of which is hereby incorporated by reference.

BACKGROUND OF THE INVENTION

1. Field of the Invention

The present invention relates to an optical measurement system and a sample optical property management method, and is used in management of optical property values in manufacture of components, products, or the like.

2. Description of the Related Art

Conventionally, various products, components, or the like are manufactured in various kinds of factories. These manufactured items are shipped after product inspection or delivery inspection. Then, when these items are received at a factory, a service office, or the like, acceptance inspection or receiving inspection is performed on these items. After that, the items are sent to an assembling process, or alternatively stored in a warehouse or the like.

In recent years, the importance of color management of products has been recognized especially in the fields of painting, forming, printing, textile, and the like. Thus, the optical property value of a product is measured often in an inspection process.

That is, in a manufacturing department or a quality control department, a spectro-colorimeter, a color difference meter, or a glossmeter is used so as to measure the optical property value such as color and gloss of a product. Then, on the basis of the measurement data obtained in this measurement, acceptance or rejection determination is performed in the product inspection.

In the color management in such product inspection, in many cases, a reference product is set up for each of various kinds of products. In this case, for each product, reference data of the reference product is recorded and stored in an inspection file. Then, in the inspection process, an inspector checks each product flowing down along the product line, and actually measures the optical property value of the product. Then, after finding out the reference data of the product from the file, the inspector compares the found out reference data with the measurement data, and thereby determines acceptance or rejection.

Further, as for the method of setting up the reference data, a method has been proposed that employs means for measuring the color value of a reference article by using a plurality of color sensors and then registering the colorimetry value as a reference color value and means for searching for already registered reference color data, so that the setting of the reference color data is performed using any one of the two kinds of means.

Conventionally, when the products flowing down along the line are of the same kind, or alternatively when only a few kinds of products flow down along the line, the reference data for these products can easily be acquired in advance, and hence the measurement data can easily be compared with the reference data so that their acceptance or rejection can easily be determined.

Nevertheless, generally, in a product line where a large number of kinds of products are treated, in many cases, a variety of products flow down irregularly in quantity and timing. Thus, in this case, much effort and time are necessary for finding out the reference data corresponding to each product flowing down, from among a large volume of the reference data. This reduces significantly the working efficiency.

Further, in some cases, even the same kind of products have a difference in the allowable color variance depending on the destination. In this case, the use of simple colorimetry data as reference data can be insufficient for determining acceptance or rejection.

Further, the products under the color evaluation have a large variety in the shape and the surface state, and hence the condition for measuring the colorimetry value also has a large variety. Thus, in some cases, the measurement need be performed under a product-proper measurement condition depending on the attribute of the product.

Such variety of measurement conditions includes: an observation field of view condition (a 2-degree field of view or a 10-degree field of view), an observation light source (light sources such as D65/A/C); the presence or absence of influence of regular reflected light (SCI/SCE); the evaluation of fluorescence color (the presence or absence of excitation light); the measurement portion of the product; and the number of times of measurement (one-time measurement or multiple time measurement).

Thus, in such color management, a large variety is present in the operation of setting and measurement, that is, in the setting of a measurement condition into the colorimeter, the operation of calibration, the setting of a measurement method, the setting of display contents, and the like. This has caused a problem that a mistake can occur in the operation.

SUMMARY OF THE INVENTION

A main object of the present invention is to provide an optical measurement system and a sample optical property management method in which even in a case that a wide variety of samples such as products and articles flow down in an irregularly mixed manner, each sample is easily and rapidly made to correspond to its corresponding reference data or measurement condition, so that acceptance or rejection determination can be performed easily and rapidly.

The main object of the present invention is achieved by providing an optical measurement system which manages whether an optical property of a sample falls within a predetermined management range. The optical measurement system comprises measuring device which measures the optical property value of the inspected sample, reader which reads an attribute identification information of an identification tag attached to the inspected sample, storage section which stores optical property management information concerning a plurality of kinds of samples each in a manner corresponding to attribute identification information of each sample, data control section which reads out from said storage section the optical property management information corresponding to the attribute identification information of the sample read by said reader, and determination section which receives the optical property management information from said data control section as well as the optical property value of the sample from the measuring device, compares the optical property management information with the optical property value of the sample, and determines whether the optical property value falls within an allowable range in the optical property management information.

These and other objects, advantages and features of the invention will become apparent from the following description thereof taken in conjunction with the accompanying drawings, which illustrate specific embodiments of the invention.

BRIEF DESCRIPTION OF DRAWINGS

These and other objects, advantages and features of the invention will become apparent from the following description thereof taken in conjunction with the accompanying drawings in which:

FIG. 5 is a diagram showing an example of a destination file;

DESCRIPTION OF THE PREFERRED EMBODIMENTS

Embodiments of an optical measurement system according to the invention are described below with reference to the accompanying drawings.

First Embodiment

Figure 1:
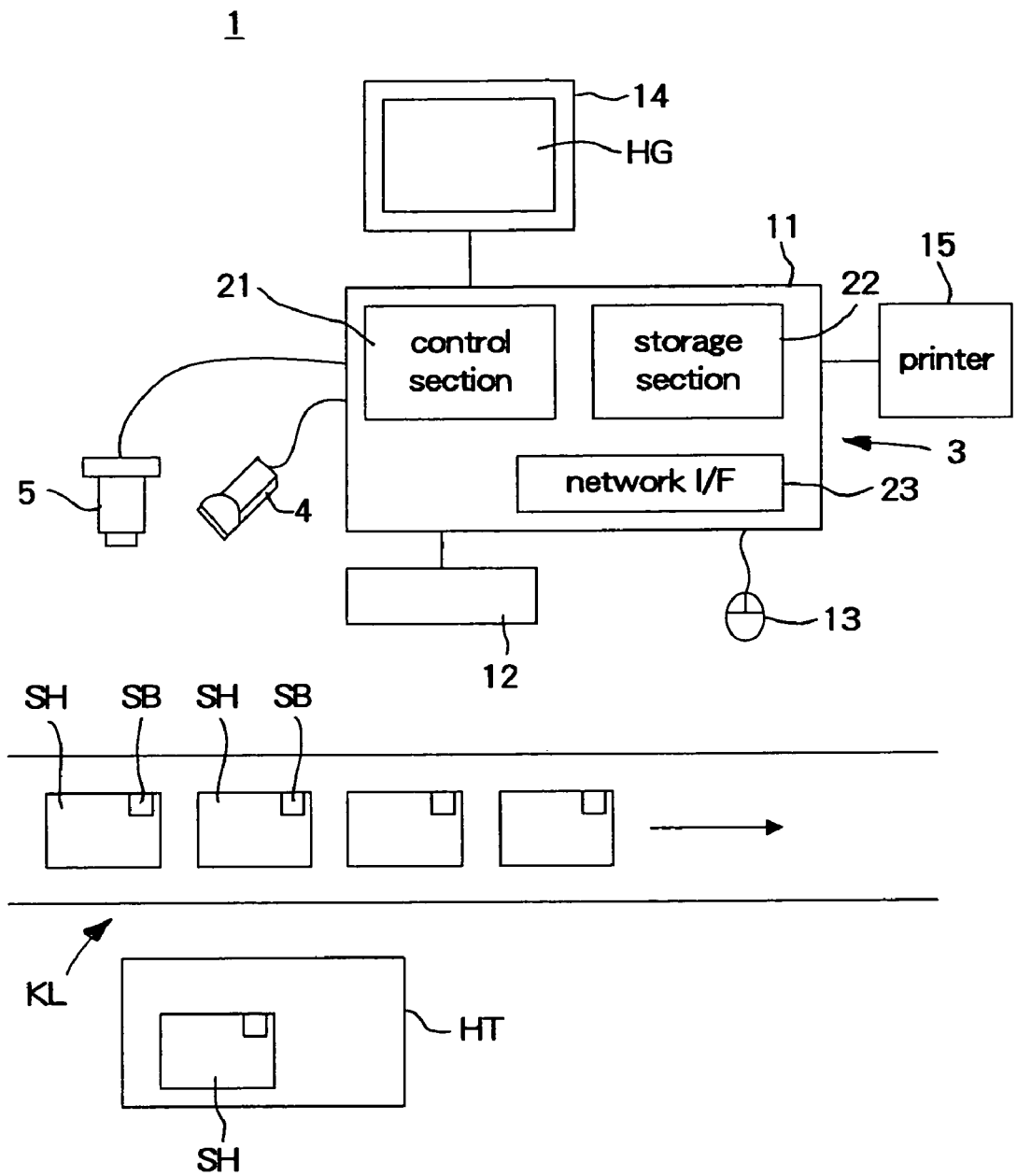
FIG. 1 is a diagram showing a schematic configuration of an optical measurement system according to a first embodiment of the invention.
Figure 2:
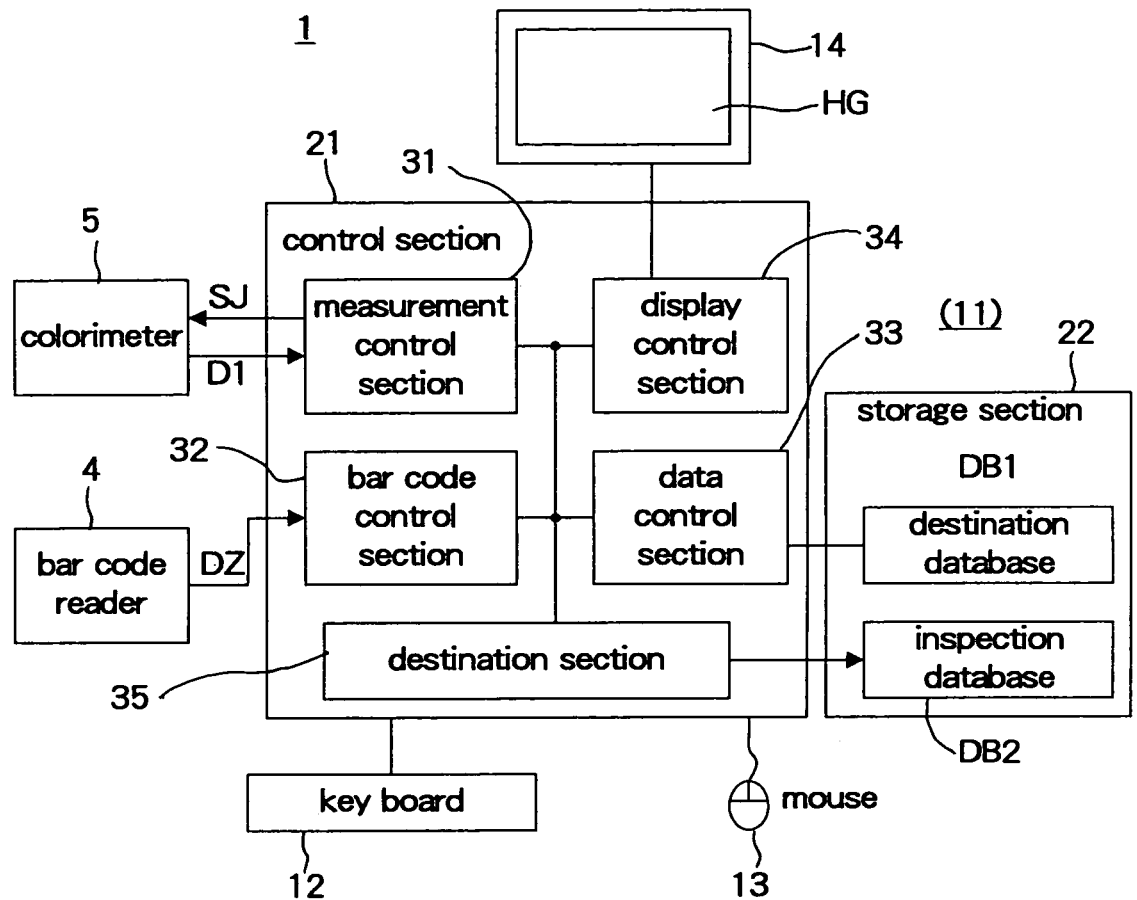
FIG. 2 is a block diagram showing a functional configuration of an optical measurement system.
Figure 3:
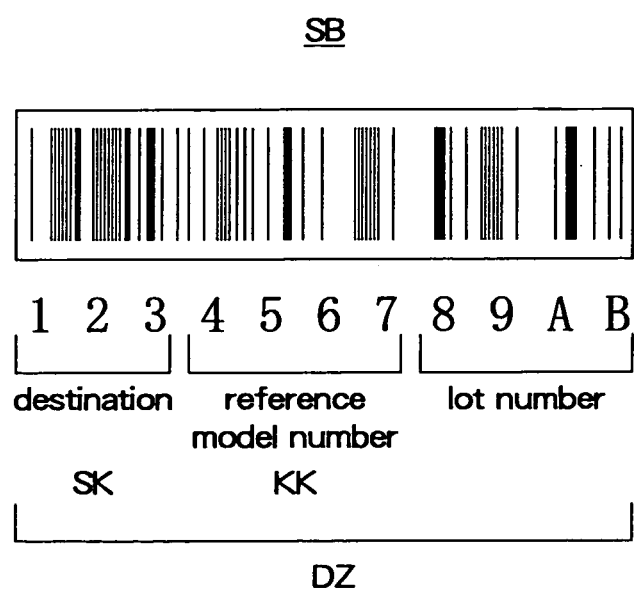
FIG. 3 is a diagram showing the configuration of a bar code attached to a product.
Figure 4:
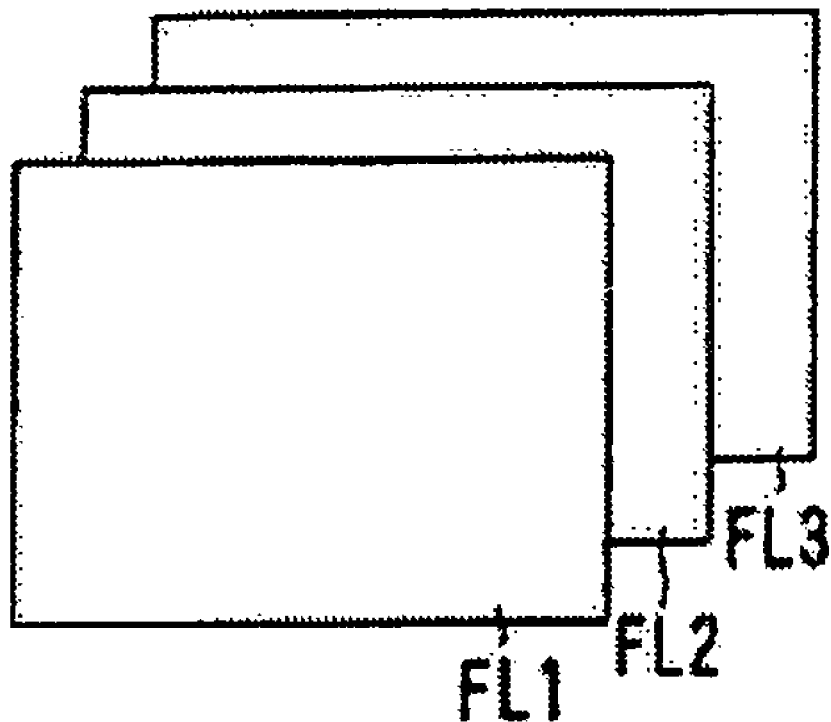
FIG. 4 is a diagram showing a schematic configuration of a destination database.
Figure 6:
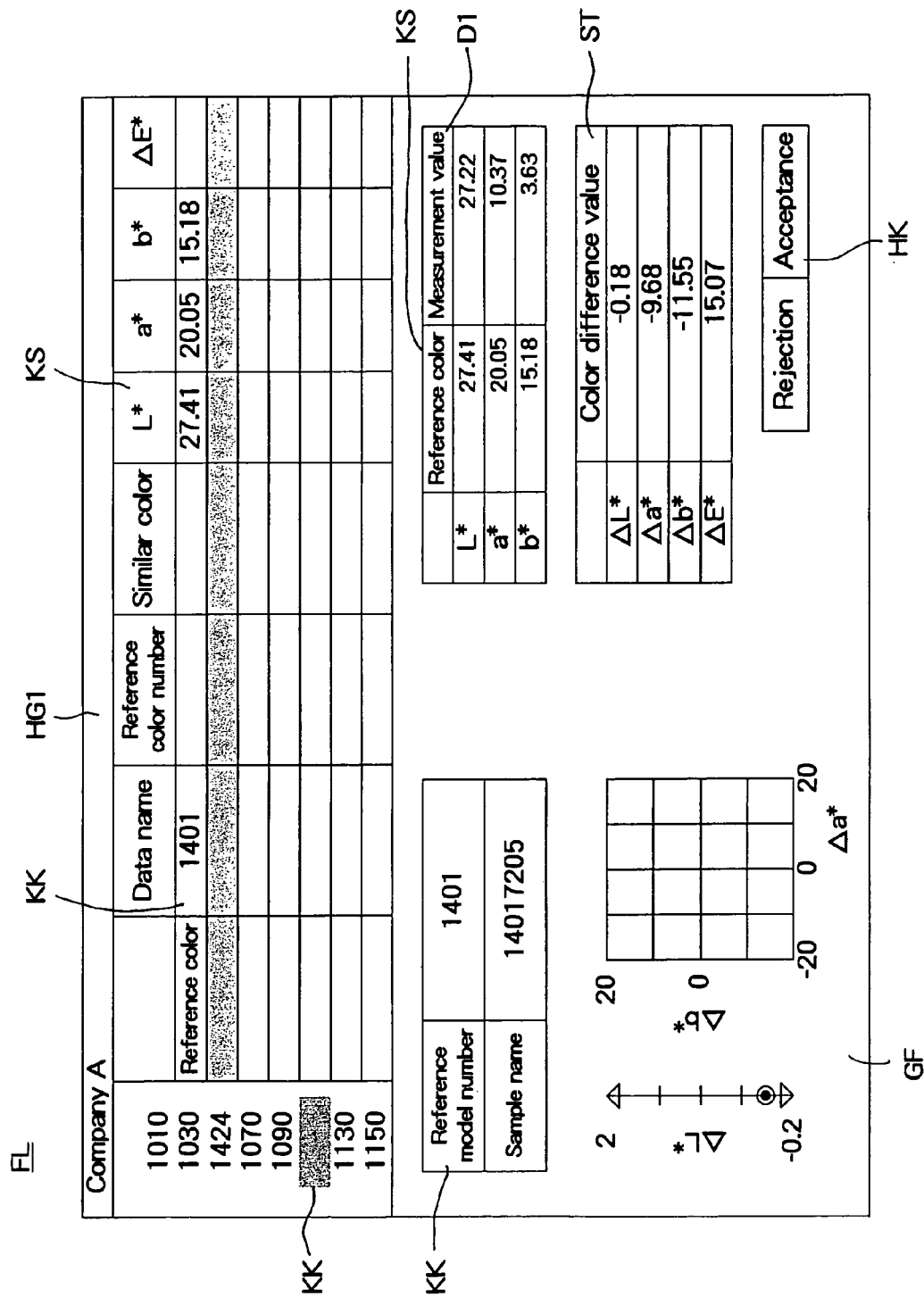
FIG. 6 is a diagram showing an example of an inspection screen displayed on a display plane.
Figure 7:
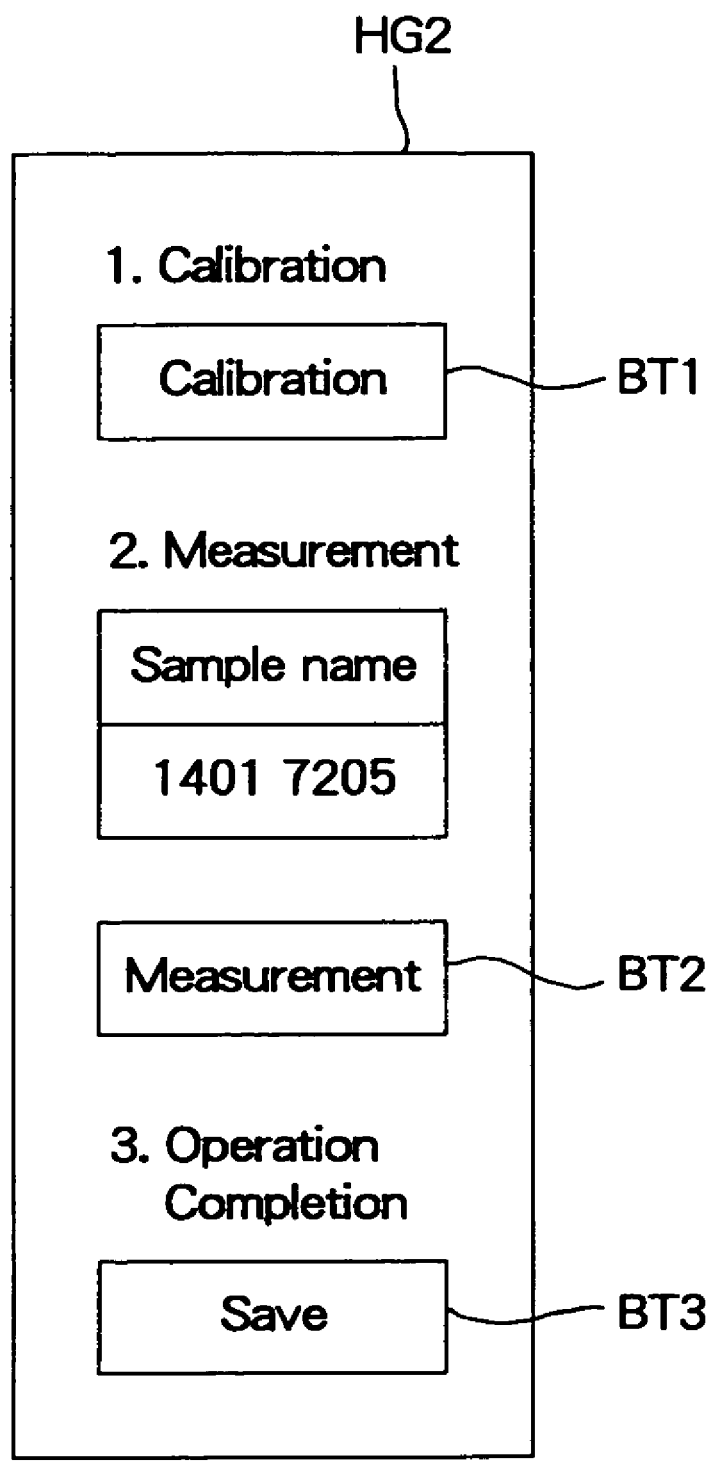
FIG. 7 is a diagram showing an example of an operation screen displayed on a display plane.

FIG. 1 is a diagram showing a schematic configuration of an optical measurement system 1 according to a first embodiment of the invention. FIG. 2 is a block diagram showing a functional configuration of the optical measurement system 1. FIG. 3 is a diagram showing the configuration of a bar code attached to a product. FIG. 4 is a diagram showing a schematic configuration of a destination database DB1. FIG. 5 is a diagram showing an example of a destination file FL. FIG. 6 is a diagram showing an example of an inspection screen HG1 displayed on a display plane. FIG. 7 is a diagram showing an example of an operation screen HG2 displayed on a display plane.

In this embodiment, the invention is applied to a process of inspecting a product SH manufactured in a factory. Thus, the sample to be inspected is called a "product".

In FIG. 1, the optical measurement system 1 comprises a computer system 3, a bar code reader 4, and a colorimeter 5.

The computer system 3 comprises: a main unit 11; an input devices such as a keyboard 12 and a mouse 13; a display 14; and a printer 15. This computer system 3 may be composed of a personal computer, a workstation, or the like.

The main unit 11 comprises: a CPU; memories such as a ROM and a RAM; a hard disk unit; various drive units; a communication interface; various peripheral circuits; and a control circuit. The hard disk unit stores: a destination database that contains optical property, management information of a large number of products SH together with their attribute identification information; and an inspection database that contains the measurement data, the inspection result, and the like of the products SH. The data of these databases are transmitted and copied between the hard disk unit and the memory, so that databases having the same contents are generated in a later described storage section 22 formed in the memory. Further, software (color management software) for the optical measurement and the optical property management of the products is installed in the hard disk unit. This software is appropriately read out into the memory, and then executed on the CPU. Furthermore, the memory stores various parameters, calculation formulas, and the like, when necessary. As a result of these functions, a control section 21 and a storage section 22 are formed in the main unit 11. Further, the main unit 11 is connected to an external network via the network interface 23, and thereby capable of transmitting and receiving various data and programs including the color management software. Furthermore, the main unit 11 can be connected to a portable recording unit (not shown). This recording unit permits the access to a recording medium such as a CD-ROM, a magneto-optical disc, a memory chip, and a memory card for transmitting and receiving various data and programs including the color management software. The optical property management information includes an optical property management value, a measurement condition, and other information.

The keyboard 12 and the mouse 13 are used by a user for inputting various instructions and commands through a screen displayed on the display plane HG of the display 14, as well as for inputting various data and commands to the main unit 11. The display plane HG of the display 14 displays an inspection screen and an operation screen described later, as well as various data, characters, and images.

As shown in FIG. 1, the optical measurement system 1 is installed in the vicinity of a product inspection line KL of a factory. Along the product inspection line KL, a large number of various products SH flow down. To each product SH, an identification tag SB is attached that records the attribute identification information of the product SH. That is, the product SH and the identification tag SB are in one-to-one correspondence so that each product SH is managed on the basis of the individual identification tag SB.

In the first embodiment, the identification tag SB is a bar code. In the product inspection line KL, the identification tag SB of each product SH is read by the bar code reader 4, while the optical property value thereof is measured by the colorimeter 5. At that time, the control section 21 reads out from the storage section 22 the optical property management information corresponding to the attribute identification information of the product SH under the inspection, then compares the read out optical property management information with the optical property value of the product SH measured by the colorimeter 5, and then determines whether the optical property value falls within the allowable range in the optical property management information. The determination result is displayed on the display plane HG of the display 14, stored into the inspection database, and outputted to the outside via the network interface 23.

Further, a revolving warning lamp, a buzzer, and the like may be provided so that when the determination result is "rejection", the revolving warning lamp and the buzzer may be turned ON.

When the inspection result of the product SH is "rejection", the product SH is moved to a rejection shelf HT manually by an inspector or automatically by a robot arm. The rejection shelf HT may be a simple table or box, or alternatively a conveyor of various types.

As shown in FIG. 2, during the execution of the program in the main unit 11, the control section 21 comprises a measurement control section 31, a bar code control section 32, a data control section 33, a display control section 34, and a determination section 35. Further, the storage section 22 comprises a destination database DB1 and an inspection database DB2.

On the basis of the optical property management information corresponding to the attribute identification information of the target product SH read out from the storage section 22, the measurement control section 31 sets up the measurement condition of the colorimeter 5. Further, the measurement control section 31 reads and temporarily stores the measurement data (optical property value) D1 outputted from the colorimeter 5.

The bar code control section 32 controls the bar code reader 4, and thereby reads and temporarily stores the read out data (attribute identification information) DZ outputted from the bar code reader 4 having read the identification tag SB attached to the target product SH.

The data control section 33 controls the destination database DB1 and the inspection database DB2, and thereby writes data into these databases or reads out data or a file. The display control section 34 edits data to be displayed as various screens on the display plane HG of the display 14, and thereby updates the screen. The determination section 35 compares the optical property management value of the target product SH read out from the destination database DB1 with the optical property value of the target product SH measured by the colorimeter 5, and thereby determines the acceptance or rejection of the product SH.

In FIG. 4, the destination database DB1 is a set of destination files FL1, 2, 3, . . . each generated for each destination SK. The destination SK indicates a destination to which a product SH manufactured in the factory is to be delivered. An optical property management value of every product SH is defined for each destination SK, and then recorded as a destination file FL.

FIG. 5 shows a destination file FL for "Company A" which is a specific destination. The destination file FL contains items such as a serial number TB, a reference model number KK, a reference color value set KS, and a management width set KH.

The reference model number KK indicates a set of products SH having the same optical property management information. That is, products SH of the same kind have obviously the same optical property management information. However, even products SH of different kinds are managed under the same optical property management information, if these products have the same reference model number KK. In contrast, if products SH of the same kind are used in different applications or in different portions, these products are provided with different reference model numbers KK corresponding to their usage conditions, and hence managed under different optical property management information. In this sense, the destination file FL describes the specification for each destination SK or each application.

The reference color value set KS indicates a reference value set of color for the product SH specified by each reference model number KK. The reference color value set KS is set up for the data $L^*$, $a^*$, and $b^*$ of the $L^*a^*b^*$ color system (referred to as "Lab color system" in some cases, hereafter). However, the reference color value set KS may be expressed in another color system such as $L^*u^*v^*$, or alternatively in terms of spectral reflectance or spectral transmittance. Further, the optical property value may be a gloss value, an optical density value, a refractive index, or the like.

The management width KH indicates an allowable range with respect to the reference color value KS. As for the management width set KH, allowable limit values $\Delta L^*$, $\Delta a^*$, $\Delta b^*$, and $\Delta E$ are set up for each data $L^*$, $a^*$, $b^*$, and for an overall evaluation value E.

Although not shown in the figure, in the destination file FL, a measurement condition set SJ to be set into the colorimeter 5 for each reference model number KK. The measurement condition set SJ includes, for example, the number of times of measurement, a measurement method (how to press the head against the product SH, a portion of pressing, and an area or region of pressing), a light source used, the inclusion or exclusion of a glossy item. Further, when a measuring instrument other than the colorimeter 5 is used, the measurement condition SJ includes: the type or model name of the measuring instrument; and a measurement method to be used. In such a measurement condition set SJ, a condition necessary as the internal condition of the colorimeter 5 is automatically set up at the time of measurement. A condition serving as guidance for the inspector is displayed in a guidance screen appropriately. For example, a portion of pressing of the head and an area or region of the pressing are displayed together with an image of the product SH as a measurement method in the guidance screen in the form of a CG.

As shown in FIG. 3, in the bar code of the identification tag SB, the first three digits specify the destination SK. The next four digits specify the reference model number KK. The last four digits specify the lot number. This configuration of the bar code is publicly known and in accordance with one of various standards.

Such an identification tag SB is attached to each product SH. In this embodiment, each product SH is an exterior casing of a portable phone. However, the invention is applicable to vary kinds of products SH such as various products or components, metal goods, synthetic resin products, and sheet like materials.

Next, described below are: a method of inspecting a product SH by means of the optical measurement system 1; and the operation of the optical measurement system 1.

When the optical measurement system 1 starts up, an inspection screen HG1 shown in FIG. 6 and an operation screen HG2 shown in FIG. 7 are displayed on the display plane HG of the display 14. However, in the inspection screen HG1 at this stage, no measurement data D1 and no determination result HK is displayed, or alternatively data of the previous inspection is displayed. The operation screen HG2 is displayed simultaneously on the right of the inspection screen HG1. However, these screens may be displayed in different windows with each other.

First, in the operation screen HG2 shown in FIG. 7, a calibration button BT1 is clicked. In response, zero calibration, white calibration, and the like are performed.

Then, in the product inspection line KL, an inspector performs inspection for each of the products SH flowing down by using the optical measurement system 1. First, the bar code reader 4 reads the identification tag SB attached to a product SH. At that time, in order that the timing of reading of the identification tag SB should be specified, an input button provided in the bar code reader 4 may be operated. Further, the name of the product SH and the like may be inputted through the keyboard 12.

The data (attribute identification information) DZ read out from the identification tag SB is inputted to the bar code control section 32 of the control section 21. In response, the reference model number "1401" and the lot number "7205" specified in the attribute identification information DZ are displayed in the field of "sample name" which is an editing box in the operation screen HG2.

After that, the colorimeter 5 is pressed against the product SH, and then a measurement button BT2 in the operation screen HG2 is clicked. In response, the data control section 33 accesses the destination database DB1, and thereby searches for a destination file FL of the destination specified by the attribute identification information DZ. Then, the data control section 33 reads and opens the found out destination file FL. The display control section 34 displays a screen corresponding to the contents of the destination file FL. Further, the measurement control section 31 sets up into the colorimeter 5 the contents of the measurement condition SJ specified in the destination file FL.

When the destination file FL is opened, the display plane HG is updated into a screen HG1 shown in FIG. 6. Further, when the measurement is performed actually, the measurement data D1 and the like are displayed.

In FIG. 6, various reference model numbers KK are displayed in the upper left part of the screen HG1. Among these, the reference model number KK "1401" of the present target product SH is selected and highlighted. On the right of this, the reference color value set KS of the selected reference model number "1401" is displayed. Further, displayed in the lines below are: the data name (sample name) "14017205" generated by the reference model number and the lot number of the target product SH; the measurement data D1; and the like.

In the central left part, the reference model number. "1401" and the lot number of the target product SH are shown. In the central right part, the contents of the reference color value KS are displayed. On the right of this, the actual measurement data D1 measured by the colorimeter 5 is displayed. In this example, the displayed reference color value set KS is "27.41", "20.05", and "15.18" for L*, a*, and b*, respectively. The displayed measurement data D1 is "27.22", "10.37", and "3.63".

Furthermore, displayed in the part below is the color difference value set ST which is the difference between the standard color value set KS and the measurement data D1 with respect to L*, a*, b*, and the overall evaluation value E. Each color difference value ST is expressed by each of the following formulas.

$$\Delta L^* = LD - LK$$

$$\Delta a^* = aD - aK$$

$$\Delta b^* = bD - bK$$

$$\Delta E = [(\Delta L^*)^2 + (\Delta a^*)^2 + (\Delta b^*)^2]^{1/2}$$

Here, LD, aD, and bD denote measurement data D1 for L*, a*, and b*. Further, LK, aK, and bK denote reference color values KS for L*, a*, and b*.

The result HK of the acceptance or rejection determination for the target product SH is displayed in the part below. This determination of acceptance or rejection is performed on the basis of whether $\Delta L^*$, $\Delta a^*$, $\Delta b^*$, and $\Delta E$ described above fall within the management width KH defined in the destination file FL. In this example, the determination result HK is "acceptance".

In the lower left part of the inspection screen HG1, the color difference value set ST is displayed in the form of a graph GF. That is, $\Delta L^*$ is plotted as a double circle at a corresponding position along a vertical axis shown in the left end part. Further, $\Delta a^*$ and $\Delta b^*$ are plotted as a double circle at a corresponding position on the $\Delta a^* \cdot \Delta b^*$ plane on the right.

As such, when the measurement button BT2 is clicked, measurement of the color difference value ST of the product SH is performed automatically. Further, the measurement data D1 is acquired, and then the measurement data D1 is compared with the reference color value KS. Then, on the basis of the management width KH, determination is performed automatically.

In the case that the measurement is performed multiple times for a single product SH, the measurement position of the calorimeter 5 is changed, and then the measurement button BT2 is clicked. At each time, the newest measurement data D1 is displayed in the inspection screen HG1, while a plurality of color difference value sets ST are plotted in the graph GF. This allows the inspector to understand intuitively the status of the color difference value ST.

Then, in the operation screen HG2, when a save button BT3 is clicked, the measurement data D1 and the determination result HK of the product SH are saved into the destination file FL.

When the determination result HK is "acceptance", the product SH is left to flow down along the product inspection line KL. At that time, an acceptance seal may be attached. When the determination result HK is "rejection", the product SH is moved to the rejection shelf HT.

Inspection in a similar procedure is performed on the next target product SH. The inspection screen HG1 is updated for the inspection of each product SH.

Next, the procedure of operation of the optical measurement system 1 is described below with reference to a flow chart.

Figure 8:
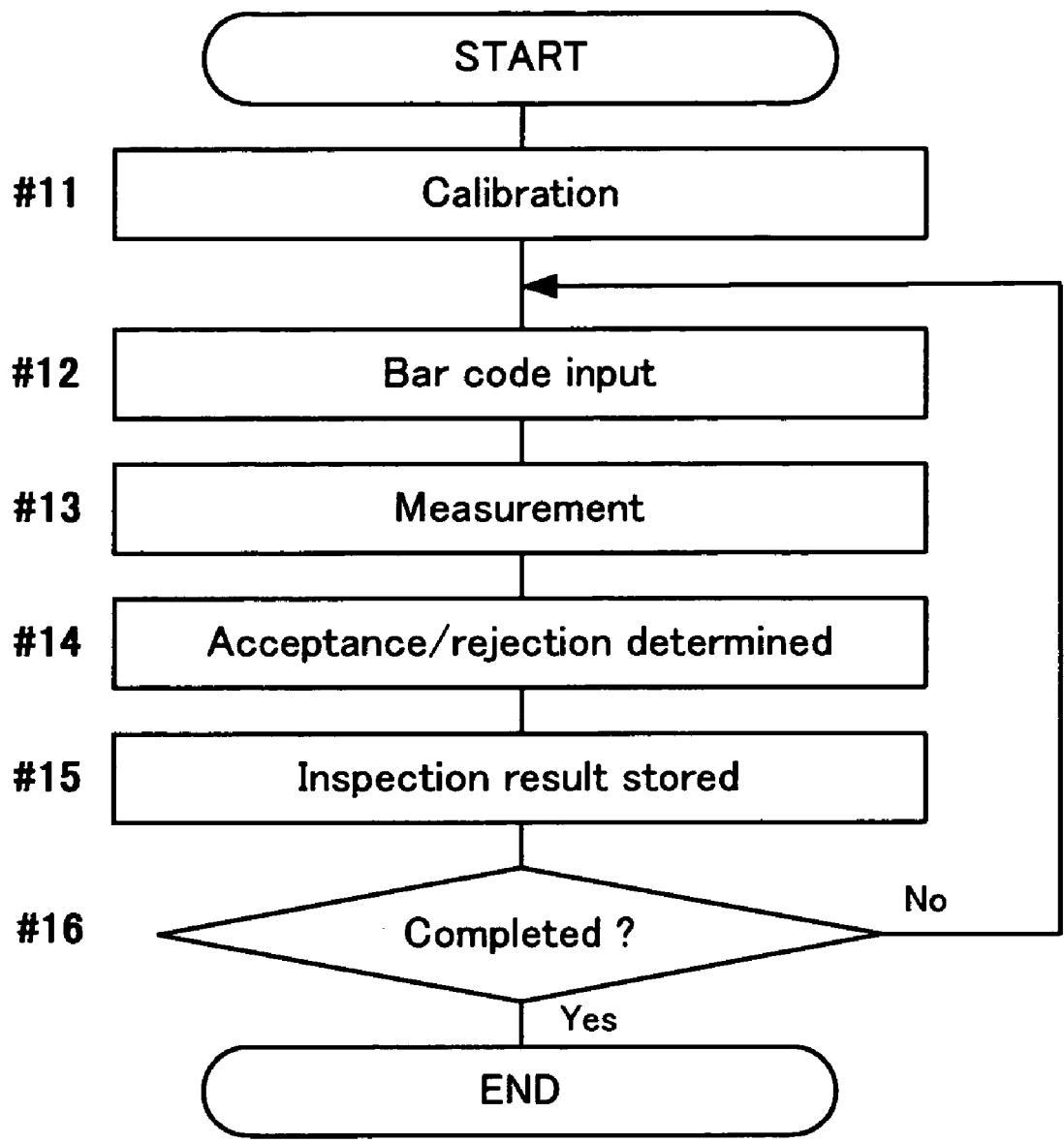
FIG. 8 is a flow chart showing an outline of procedure.
Figure 9:
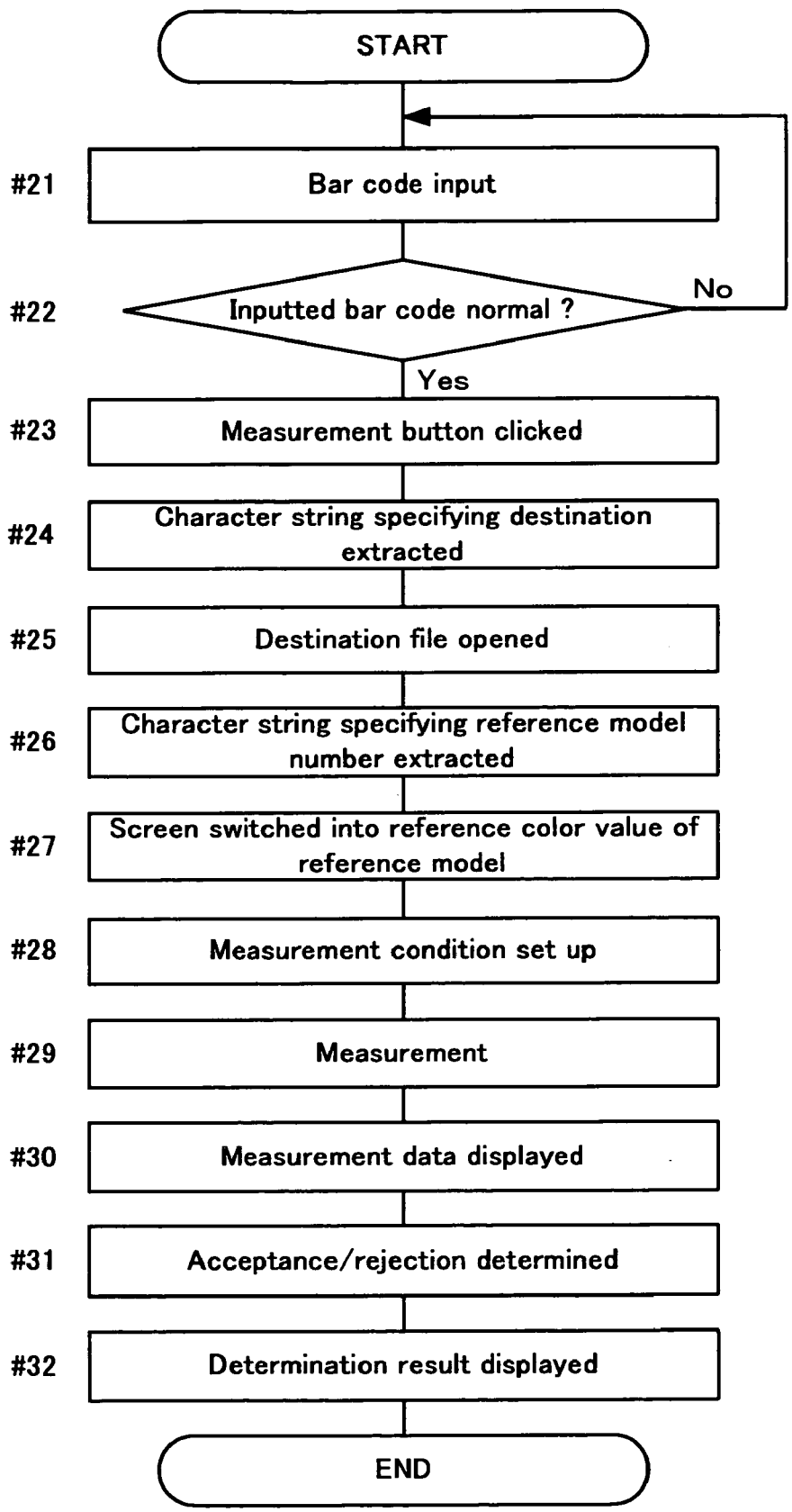
FIG. 9 is a flow chart showing the detail of a part of FIG. 8.

FIG. 8 is a flow chart showing an outline of procedure. FIG. 9 is a flow chart showing the detail of steps #12-#14 of FIG. 8.

In FIG. 8, calibration is performed first (#11). Then, a bar code is inputted (#12). Then, measurement is performed on the product SH (#13). Then, acceptance or rejection is determined (#14). After that, the inspection result is stored into the destination file FL (#15). These steps are repeatedly until these operation and processing have been completed for a large number of the products SH (#16).

In FIG. 9, when the bar code is inputted (#21), and when the inputted bar code is not normal (No at #22), the input is performed again. For example, when a bar code has been inputted but actual data is not present, or alternatively when the data is in a format that cannot be treated by the system, the situation is determined as abnormal.

When the measurement button BT2 is clicked (#23), a character string specifying a destination is extracted from the inputted bar code (#24). On the basis of the destination, a destination file FL is opened (#25). Then, a character string specifying a reference model number KK is extracted from the bar code (#26). The inspection screen HG1 is switched in correspondence to the reference color value KS of the reference model number KK (#27). A measurement condition is set up (#28). Measurement is performed on the product SH (#29). The measurement data D1 is displayed in the inspection screen HG1 (#30). Acceptance or rejection is determined (#31). Then, the determination result is displayed (#32).

According to the optical measurement system 1 described above, even in the case that a wide variety of products SH flow down in an irregularly mixed manner, the bar code reader 4 reads the identification tag SB provided to the product SH, and then the control section 21 easily and rapidly establishes the correspondence between each product SH and its corresponding reference color value KS. Further, acceptance or rejection determination is automatically performed easily and rapidly. Furthermore, the measurement condition SJ of the product SH is automatically read from the destination file FL, and then set up automatically into the calorimeter 5. This avoids the necessity that an inspector manually sets up the measurement condition for each product SH. This improves the work efficiency significantly.

In the destination database DB1, a file is generated for each destination. Thus, when a destination is extracted from the attribute identification information DZ read out from the identification tag SB, and when on the basis of the destination, a destination file FL is read out, the reference color value KS corresponding to a reference model number KK is acquired easily and rapidly.

Further, a destination file FL is generated for each destination. This permits easy management of the reference color value KS, the measurement condition SJ, and the like which are different for each destination. This allows the inspector to easily understand the relation between the product SH and the reference color value KS.

The attribute identification information DZ of the identification tag SB contains information for identifying the destination, that is, product distribution information. This allows the optical measurement system 1 to manage the destination of the product SH, and permits easy management of the subsequent product distribution of the product SH. Further, the management width KH for the acceptance or rejection determination can be set up, revised, or managed easily depending on the destination.

The method of outputting the determination result may be to write into an internal or external memory, to write into an IC tag, to display on a display plane of a display, to print through a printer, or to transmit to another apparatus via a communication line. The sample may be an item of a wide variety such as a product, a component, a trial product, and a test article.

Second Embodiment

Next, an optical measurement system 1B according to a second embodiment is described below.

In the optical measurement system 1B, an IC tag is used in place of the bar code as the identification tag SB. Thus, in place of the bar code reader 4, a read and write unit 4B is used that can transmit and receive data to and from the IC tag. Similarly to the case of the bar code, the IC tag stores in advance the attribute identification information DZ. The difference of the IC tag from the bar code is that the measurement data D1, the determination result HK, and the like can be recorded into the IC tag of the product. The other points are the same as the optical measurement system 1 of the first embodiment. Thus, description of these points has already been given in the description and the figures of the first embodiment, and hence is omitted here. The following description is focused on the difference.

Figure 10:
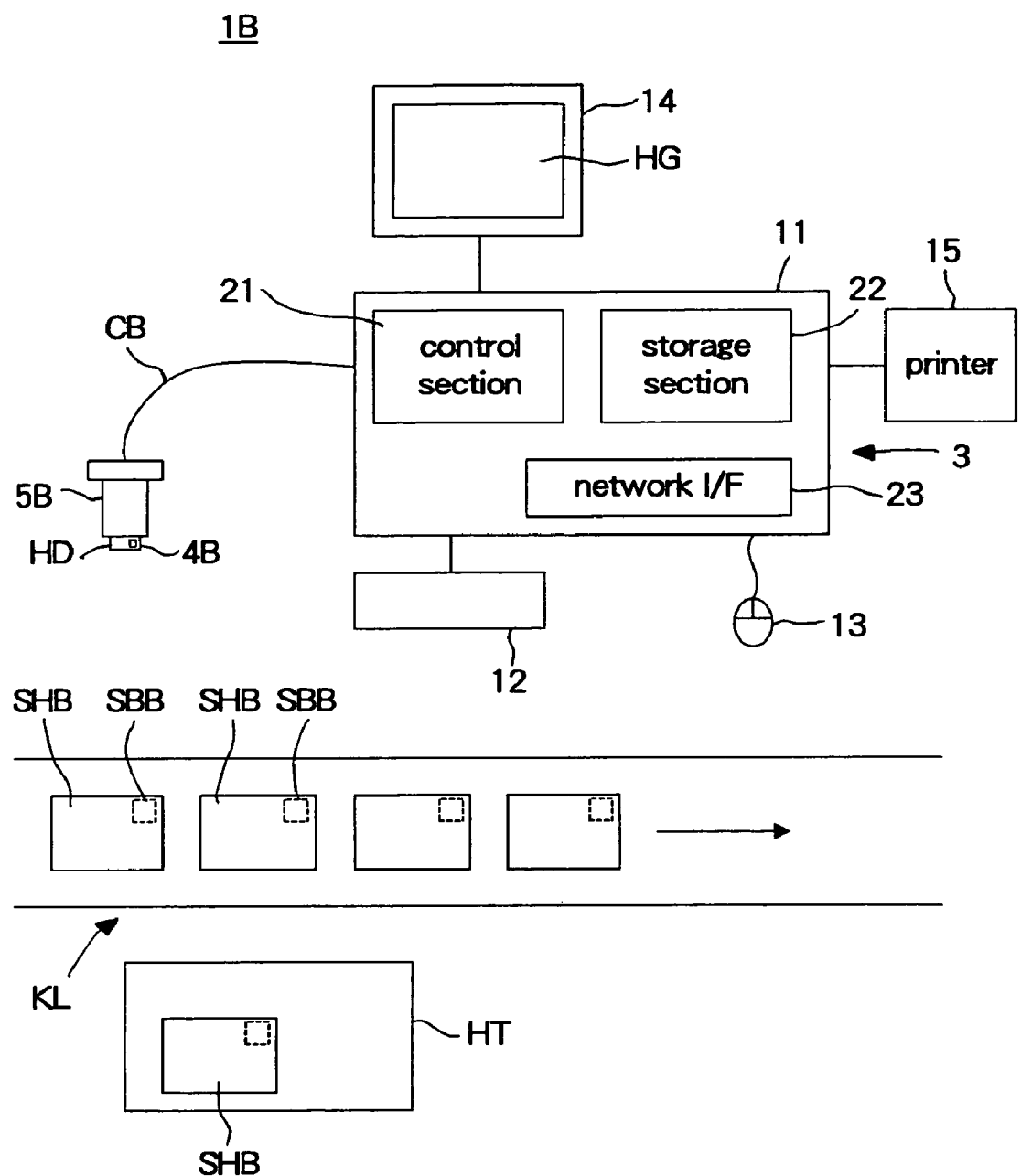
FIG. 10 is a diagram showing a schematic configuration of an optical measurement system according to a second embodiment.
Figure 11:
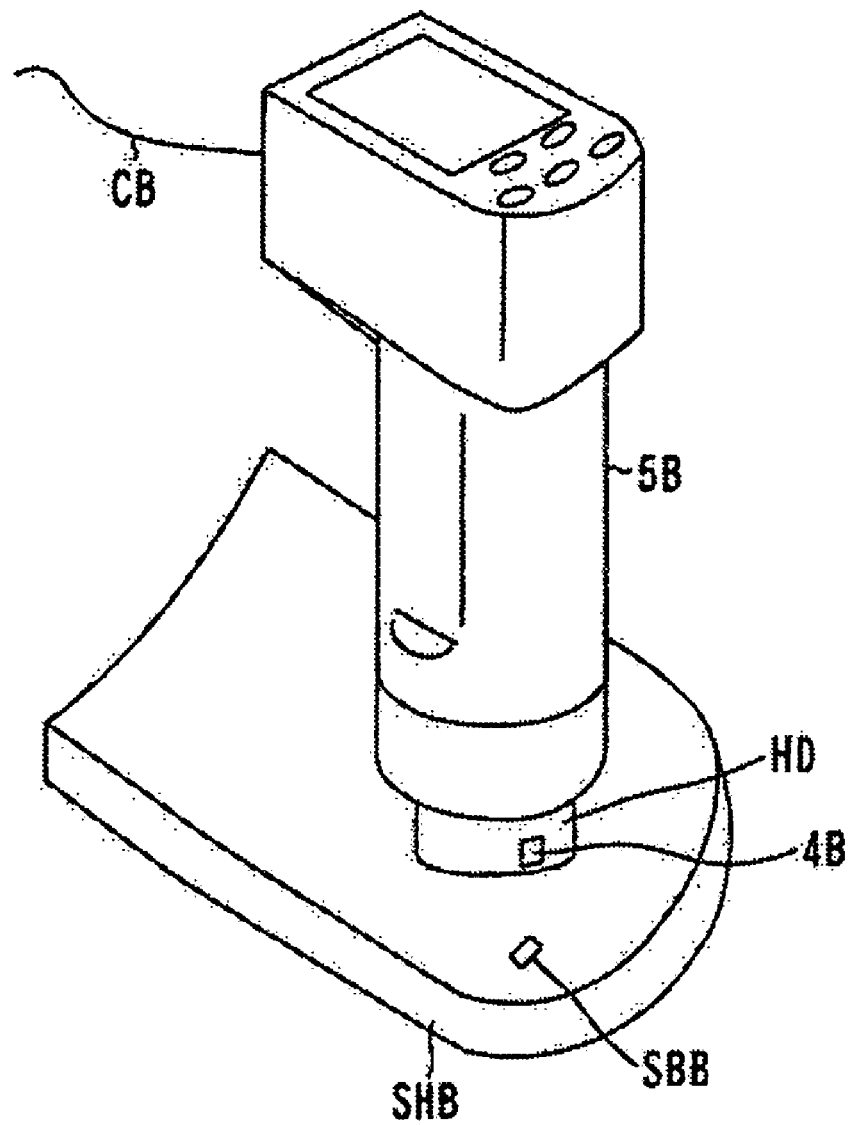
FIG. 11 is a perspective view showing a read and write unit and a colorimeter according to a second embodiment.
Figure 12:
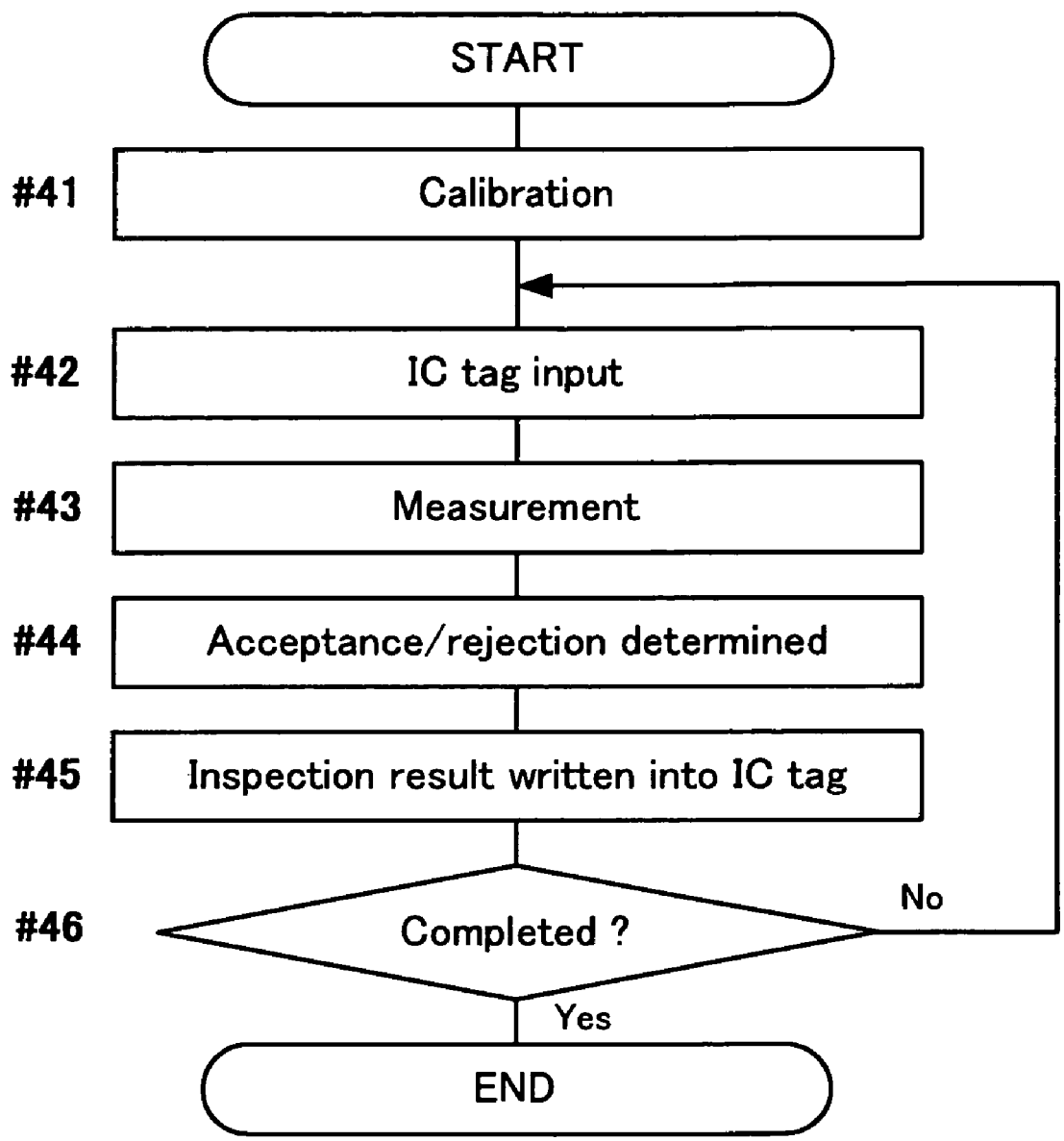
FIG. 12 is a flow chart showing an outline of procedure according to a second embodiment.

FIG. 10 is a diagram showing a schematic configuration of an optical measurement system 1B according to the second embodiment of the invention. FIG. 11 is a perspective view showing a read and write unit 4B and a colorimeter 5B used in the second embodiment. FIG. 12 is a flow chart showing an outline of procedure according to the second embodiment.

As shown in FIGS. 10 and 11, the read and write unit 4B is provided in the measuring head HD of the colorimeter 5B. The read and write unit 4B can transmit and receive data to and from the IC tag SBB by wireless. Such a read and write unit 4B and an interface used here may be any one of various publicly known devices. The signals outputted from the read and write unit 4B and the colorimeter 5B and the signals inputted to these devices are exchanged with the main units 11 through a bundled cable CB.

As such, the read and write unit 4B is provided in the measuring head HD of the colorimeter 5B. Thus, when the measuring head HD of the colorimeter 5B is made close to the product SHB for the measurement, the read and write unit 4B can read or write information from or into the IC tag SBB. This simplifies the operation significantly.

For example, when the colorimeter 5B measures the optical property value, the read and write unit 4B reads the attribute identification information DZ from the IC tag SBB. Almost at the same time, acceptance or rejection can be determined. Then, the determination result HK can be written into the IC tag SBB in real time. This simplifies the operation or the processing significantly. Further, this configuration permits easy automation of the access from the read and write unit 4B to the IC tag SBB and the measurement in the calorimeter 5B.

The product SHB shown in FIGS. 10 and 11 is, for example, an exterior casing of a portable phone. In the product SHB, the IC tag SBB is embedded that records the attribute identification information DZ of the product SHB. The IC tag SBB can be arranged such as not to be seen from the outside, and hence the presence of the IC tag SBB can be prevented from being known. This reduces the possibility that an unauthorized person uses the information in the IC tag SBB.

The IC tag SBB can store as the attribute identification information DZ the destination, the reference model number KK, and the lot number described above, as well as the name of the product, the name of the product color, the measuring instrument to be used, the reference value name, the color system, the manufacturer, and the date of manufacture. Further, data such as the reference color value KS, the management width KH, and the measurement condition SJ may be recorded that is stored in the destination file FL. Furthermore, after the inspection, that is, the measurement, is performed, data such as the inspection date, the measurement data D1, the determination result HK, and the term of validity of the measurement data D1 is written into the IC tag SBB.

Further, the IC tag SBB may store an inspection certificate, a traceability system, a calibration (repair) history, and the like as history information of the product SHB. In a reference product or a product for calibration, when information such as the inspection certificate, the traceability system, and the pricing history is stored in addition to the values used as the reference, the requirement of ISO and the like is satisfied.

In FIG. 12, calibration is performed first (#41). Then, the identification data recorded in the IC tag SBB is read out (#42). Then, measurement is performed on the product SHB (#43). Acceptance or rejection is determined (#44). The inspection result is stored into the destination file FL, and written into the IC tag SBB via the read and write unit 4B (#45). These steps are repeatedly until these operation and processing have been completed for a large number of the products SHB (#46).

As such, when the IC tag SBB stores the measurement data D1 and the determination result HK, the measurement data D1 and the determination result HK of the product SHB are retained in a manner integrated with the product SHB. This simplifies the management significantly in comparison with the prior art case that the information is recorded on various media such as paper and a flexible disk. Further, the data or the information can easily be read out from the IC tag SBB, and thereby checked. This simplifies the use of the recorded data in a later process.

For example, the measurement data D1 and the like recorded in the IC tag SBB may be read out in a later process, and then a predetermined processing may be performed depending on the measurement data D1 of the product SHB. Such a later process may be a process immediately following the inspection process or a completely separate process independent of the inspection process.

Applications are described below for the case that the IC tag SBB is used as the identification tag SB.

(1) In the measurement of the product SHB, information is read out from the IC tag SBB. Then, acceptance or rejection is determined. At the same time, the measurement data D1 and the determination result HK is written into the IC tag SBB in real time.

(2) In order that products having similar shade should be matched with each other in the assembling process of the products SHB, the products SHB are classified or ranked on the basis of the shade. This suppresses the variance in the color of the products, and hence improves the color quality of the products SHB. Further, this avoids the occurrence of rejected articles caused by the color variance, and hence permits the use of a wider management range of the color. This improves the yield of the product SHB, and effectively reduces the occurrence of rejected articles.

(3) In the stage of delivery inspection or receiving inspection of the product SHB, the information in the IC tag SBB is read out. This permits easy checking of the acceptance or rejection according to the inspecting standard and of the value of deviation from the reference color value KS.

The configuration, the structure, the shape, the contents of processing, the processing method, the timing of processing, and the like of the entirety or a component of the optical measurement systems 1 and 1B described above can be modified appropriately without departing from the spirit of the invention.

According to the invention, even in a case that a wide variety of samples such as products and articles flow down in an irregularly mixed manner, each sample is easily and rapidly made to correspond to its corresponding reference data or measurement condition, so that acceptance or rejection determination can be performed easily and rapidly.

Although the present invention has been fully described by way of examples with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. An optical measurement system which manages whether an optical property of a sample falls within a predetermined management range, said optical measurement system comprising:
   a measuring device which measures the optical property value of the inspected sample, the optical property value being a color-related property value;
   a reader which reads an attribute identification information of an identification tag attached to the inspected sample;
   a storage section which stores optical property management information concerning a plurality of kinds of samples each in a manner corresponding to attribute identification information of each sample;
   a data control section which reads out from said storage section the optical property management information corresponding to the attribute identification information of the sample read by said reader;
   a determination section which receives the optical property management information from said data control section as well as the optical property value of the sample from the measuring device, compares the optical property management information with the optical property value of the sample, and determines whether the optical property value falls within an allowable range in the optical property management information; and
   a storing section which stores whether the optical property value falls within an allowable range in the optical property management information.

2. An optical measurement system as claimed in claim 1, further comprising:
   a display device; and
   a display control section which receives the determination result outputted from the determination section and displays the determination result on a screen of said display device.

3. An optical measurement system as claimed in claim 1, wherein said identification tag attached to the sample is a rewritable recording medium, and said determination result is written into the recording medium attached to the sample under the determination.

4. An optical measurement system as claimed in claim 1, further comprising:
   a measurement control section which sets up a measurement condition of said measuring device based on the measurement condition read out from said storage section, said measurement condition and an optical property management value being included in the optical property management information; and
   wherein said determination section determines whether the optical property value falls within the allowable range using the optical property management value corresponding to the set up measurement condition.

5. An optical measurement system as claimed in claim 1, wherein said attribute identification information includes product distribution information of the sample, and said determination section determines whether the optical property value falls within the allowable range using the optical property management information corresponding to said product distribution information.

6. An optical measurement system as claimed in claim 1, wherein said identification tag attached to the sample is a rewritable recording medium, and the reader is provided in a vicinity of a measuring head of said measuring means and capable of reading from and writing into said recording medium.

7. An optical measurement system as claimed in claim 6, further comprising:
   a reader control section which controls the reader to read the attribute identification information from said recording medium, and writes said determination result into said recording medium when the measuring device measures the optical property value of the sample.

8. An optical measurement system as claimed in claim 1, wherein said storage section has a plurality of destination files for storing the optical property management information for each destination of the sample.

9. An optical property management method which manages whether an optical property of a sample falls within a predetermined management range, said optical property management method comprising the steps of:
   attaching an identification tag recording an attribute identification information to the inspected sample;

storing in a storage device an optical property management information concerning a plurality of kinds of samples in a manner corresponding to the attribute identification information of each sample;

reading the attribute identification information from the identification tag attached to the sample by use of a reader;

measuring an optical property value of the inspected sample by a measuring device, the optical property value being a color-related property value;

reading out from said storage device the optical property management information corresponding to the attribute identification information;

comparing the optical property management information from the storage device with the optical property value of the sample from the measuring device;

determining whether the optical property value falls within an allowable range in the optical property management information; and storing a determination result.

10. An optical property management method as claimed in claim 9, further comprising the step of:

outputting a determination result on a screen of a display device.

11. An optical property management method as claimed in claim 9, wherein said identification tag attached to the sample is a rewritable recording medium; and further comprising the step of:

writing a determination result into the recording medium attached to the sample under the determination.

12. An optical property management method as claimed in claim 9, further comprising the steps of:

setting up a measurement condition of said measuring device based on the measurement condition read out from said storage device, said measurement condition and an optical property management value being included in the optical property management information; and determining whether the optical property value falls within the allowable range using the optical property management value corresponding to the set up measurement condition.

13. A computer readable medium containing a computer executable program, said program comprising computer executable code to cause a computer in an optical measurement system to perform a method for managing whether an optical property of a sample falls within a predetermined management range, comprising the steps of:

storing in a storage device an optical property management information concerning a plurality of kinds of samples in a manner corresponding to an attribute identification information of each sample;

reading the attribute identification information from the identification tag attached to the inspected sample by a reader;

measuring an optical property value of the inspected sample by a measuring device, the optical property value being a color-related property value;

reading out from said storage device the optical property management information corresponding to the attribute identification information;

comparing the optical property management information from the storage device with the optical property value of the inspected sample from the measuring device;

determining whether the optical property value falls within an allowable range in the optical property management information; and storing a determination result.

* * * * *